(12) United States Patent
Smythe

(10) Patent No.: US 8,746,069 B2
(45) Date of Patent: Jun. 10, 2014

(54) DEVICES AND METHODS OF ULTRASOUND TIME OF FLIGHT DIFFRACTION SENSITIVITY DEMONSTRATION

(75) Inventor: Dennis Smythe, Simpsonville, SC (US)

(73) Assignee: Fluor Technologies Corporation, Aliso Viejo, CA (US)

(*) Notice: Subject to any disclaimer, the term of this patent is extended or adjusted under 35 U.S.C. 154(b) by 378 days.

(21) Appl. No.: 13/119,880

(22) PCT Filed: Feb. 12, 2009

(86) PCT No.: PCT/US2009/033915
§ 371 (c)(1),
(2), (4) Date: Mar. 18, 2011

(87) PCT Pub. No.: WO2010/047842
PCT Pub. Date: Apr. 29, 2010

(65) Prior Publication Data
US 2011/0203376 A1    Aug. 25, 2011

Related U.S. Application Data

(60) Provisional application No. 61/106,671, filed on Oct. 20, 2008.

(51) Int. Cl.
*G01N 29/024* (2006.01)
(52) U.S. Cl.
USPC .................. 73/598; 73/602; 73/627

(58) Field of Classification Search
USPC ........... 73/598, 600, 602, 620, 622, 628, 629, 73/627
See application file for complete search history.

(56) References Cited

U.S. PATENT DOCUMENTS

| | | | |
|---|---|---|---|
| 5,404,754 A | 4/1995 | Wang | |
| 5,665,893 A | 9/1997 | Smith | |
| 6,125,704 A | 10/2000 | Wang | |
| 6,640,632 B1 | 11/2003 | Hatanaka et al. | |
| 6,851,319 B2 * | 2/2005 | Ziola et al. | 73/622 |
| 7,168,322 B2 * | 1/2007 | Bardoux et al. | 73/588 |
| 7,188,526 B2 * | 3/2007 | Taylor et al. | 73/618 |
| 7,683,288 B2 * | 3/2010 | Scott et al. | 219/61.5 |
| 8,104,347 B2 * | 1/2012 | Den Boer | 73/596 |

OTHER PUBLICATIONS

Wang, Z., et al, "TOFD-Scan Imaging Based on Synthetic Aperture Focusing Technique", 17th World Conference on Nondestructive Testing, Oct. 25-28, 2008, Shanghai, China.

* cited by examiner

*Primary Examiner* — J M Saint Surin
(74) *Attorney, Agent, or Firm* — Fish & Tsang, LLP

(57) ABSTRACT

An ultrasound time-of-flight diffraction reference block has a plurality of notches that extend into the block to simulate cracks, wherein the notches have a normal and transverse orientation with respect to a test path formed on the block.

14 Claims, 2 Drawing Sheets

DEVICES AND METHODS OF ULTRASOUND TIME OF FLIGHT DIFFRACTION SENSITIVITY DEMONSTRATION

This application claims priority to our U.S. provisional application with the Ser. No. 61/106,671, which was filed Oct. 20, 2008.

FIELD OF THE INVENTION

The field of the invention is devices and methods related to instrument proving and/or calibration, especially as it relates to examination time-of-flight diffraction technique (TOFD) devices and methods.

BACKGROUND OF THE INVENTION

Non-destructive material testing for welds is well known in the art and depending on the particular welded materials and welding processes, various testing methods can be employed, including liquid penetrant testing, X-ray analysis, eddy current testing, and ultrasonic testing. While most of the currently known test methods provide reproducible and unambiguous results for many materials, ultrasonic testing (e.g., single-probe, TOFD, phased array, etc.) has proven to be particularly advantageous as the test results are typically immediately available using relatively simple equipment.

However, despite the versatility of ultrasonic testing, certain material flaws are often difficult to detect using such testing. For example, reheat cracks in heavy-walled hydrogen reactor vessels are often very small and clustered. To help improve detection of such flaws, various highly refined ultrasonic methods can be employed. For example, as described in U.S. Pat. No. 6,125,704, spectral response analysis of a suspect signal from a high-frequency angle beam transducer in pitch-catch mode is performed against a reference signal from a matching transducer that is operated in pulse-echo mode. In such methods, the signals from cracks formed by hydrogen attack will increase in amplitude with an increase in frequency, whereas no such dependence is evident from cracks due to welding defects. It should be noted that the cracks in Cr—V hydrogen reactors are considered reheat cracks. Although the cracking mechanism is not completely understood it is thought to be caused by a fracturing of the material due to stress and localized lowering of fracture toughness at a certain temperature range. Alternatively, as described in U.S. Pat. No. 5,404,754, amplitude-based and pattern-based backscatter signal analysis is used to identify and characterize defects due to hydrogen attack.

While such methods typically provide at least some improvement over conventional methods, various difficulties nevertheless remain. Among other things, the cracks caused by reheat cracking tend to be vertically oriented and transverse to the direction of the weld, and so render detection problematic where the detection employs conventional ultrasonic testing. Worse yet, as hydrogen tends to modify the fracture mechanical properties of the material, the standard flaw size requirements in the ASME Code often fail to provide adequate predictability of and confidence in proper service of such reactors.

TOFD ultrasonic testing in B-scan direction appears to provide the most sensitive and/or reliable manner of detection, however, various problems remain with such approach. For example, the sensitivity and calibration blocks pursuant to the ASME Code typically fail to replicate the response observed from actual reheat cracks for various reasons. Among other things, the fabricated flaws (side drilled holes) are not only too large to be comparable to reheat cracks, but due to the round acoustic interface also tend to reflect the energy back to the receiving probes rather than generating a weaker diffracted wave as would be the case with reheat cracks. Still further, the drilled holes in ASME blocks are arranged directly above each other, which results in a merging and confusion of the signals.

To overcome the difficulties associated with relatively large side drilled holes, smaller diameter side drilled holes may be used. However, such smaller round holes nevertheless tend to reflect the energy and generally provided unsatisfactory results. On the other hand, a series of flat bottom holes with progressively increasing distance could be used to discern lateral beam coverage. However, while the output in such tests will typically yield at least some information on lateral beam coverage, such output is limited to a single thickness plane (depth). Furthermore, replication of the response observed from reheat cracks is additionally complicated by the ASME code requirement to arrange the flaws parallel to the fusion line. In contrast, reheat cracks are typically transverse to the fusion line, which will invariably lead to a vastly different response in the TOFD output. On a finer note, the code also fails to require a sufficient number of flaws and/or to allow measurement of the lateral (width) area to thereby gain an improved understanding of the area of coverage enabled by each TOFD setup. Moreover, as the code is focused on conventional non-parallel scanning direction view, a potential lack of coverage of the entire weld width is not addressed where B-scan view in parallel scanning direction is employed. Such lack is particularly problematic where wide weld widths are tested.

Therefore, it should be readily apparent that while TOFD ultrasonic testing in B-scan direction may at least conceptually provide the most sensitive and/or reliable manner of detection for reheat crack detection, conventional sensitivity and qualification blocks dictated by the ASME Code fail to address critical issues, and such testing has not been implemented. Thus, there is still a need to provide improved devices and methods for TOFD sensitivity demonstration and calibration.

SUMMARY OF THE INVENTION

The present invention is directed to various devices and methods of TOFD sensitivity demonstration that allows validation of a TOFD set up to detect reheat cracks. Moreover, the devices and methods according to the inventive subject matter also allow correlation of signal strength/flaw size to actual reheat cracks. Consequently, the so obtained results will allow an operator to assess suspect areas with significantly improved accuracy and confidence.

In one aspect of the inventive subject matter, an ultrasound time-of-flight diffraction reference block (typically fabricated from steel) has a plurality of stepped notches within the block in perpendicular and normal direction relative to a test surface on the block. Most preferably, the stepped notches are arranged relative to each other such that a second notch does not interfere with a signal to or from a first notch. It is further preferred that welded fills are disposed between respective notches and a wall of the block to reduce or even eliminate interference from a sidewall of the block. Additionally, it is generally preferred that the test surface has a size that is sufficient to allow positioning of a TOFD setup in a laterally offset position relative to a position that is perpendicularly above the notches.

Therefore, and viewed from a different perspective, preferred ultrasound time-of-flight diffraction reference blocks will comprise a mass of material having a first surface defining a preferably planar test path, and multiple flat notches within the mass of material and disposed perpendicularly below the first surface. Most typically, at least one of the flat notches has a transverse and normal orientation relative to the test path.

Particularly contemplated blocks will also include a second surface, wherein a welded fill is disposed between a flat notch and the second surface. While not limiting to the inventive subject matter, it is typically preferred that the notches are representative of hydrogen reheat cracks, and thus will have a thickness of less than 1 mm and a depth and height of less than 5 mm×5 mm. Moreover, it is generally preferred that the flat notches are arranged in a stepwise manner along the second surface. In such devices, the flat notches most preferably have a vertical offset of between 8-12% of the height and a horizontal offset of between 12-25% of the height of the device such as not to produce interfering signals from two or more notches.

Therefore, the inventor also contemplates a method of forming an ultrasound TOFD reference block in which in one step a test surface is formed on a mass of material. In another step, a plurality of flat notches is formed within the mass of material such that the notches are perpendicularly disposed below the test surface, and wherein at least one of the flat notches has a transverse and normal orientation relative to the test path. In preferred aspects of the inventive subject matter, the flat notches are formed by electrical discharge machining, laser micromachining, or electrochemical micromachining. Such methods may also include a further step of forming a groove into the notch or first forming a groove and then a notch in the groove, wherein the groove is filled with a weld filler to so isolate the notch from the side wall of the block, and to reduce the remaining size of the notch to a surface area comparable to typical reheat cracks (e.g., 4 mm×4 mm). Creating flaw tips at upper and lower extremity that are 4 mm in length should create a diffracted wave signal comparable in amplitude (or sound pressure level) to those found in actual reheat cracks Various objects, features, aspects and advantages of the present invention will become more apparent from the following detailed description of preferred embodiments of the invention.

DETAILED DESCRIPTION

The inventors have discovered that a TOFD sensitivity demonstration block can be made in a simple and effective manner that not only allows verification of the capability of the TOFD set up to detect reheat cracks but also allows a comparison of signal strength/flaw size to actual reheat cracks. Consequently, the TOFD sensitivity demonstration blocks and methods presented herein allow for a more accurate interpretation of the test output.

Most significantly, contemplated TOFD sensitivity demonstration blocks will have a plurality of generally flat defects that extend in a direction that is perpendicular to a test path (simulating a weld), and wherein the plane of the defect is typically normal to the test path. It should be appreciated that the shape and positioning of the (typically notch shaped) defects will more accurately reflect reheat cracks caused by hydrogen attack and so allow to obtain meaningful and accurate test results and confidence in the TOFD setup. It should be noted that the exact cause of the reheat cracks is not completely understood, and may indeed not be hydrogen attack because these materials are subjected to a high preheat during fabrication and a dehydrogenation heat treatment (DHT) immediately after each weld is fabricated. Reheat cracking is only observed after intermediate stress relief (ISR) where the temperature reaches 650° C. and a suspected fault in the welding filler materials and/or flux causes a sharp dip in material toughness at that temperature. It is believed that cracking occurs at this point in the ISR due to the stress exceeding material strength.

Figure 1:
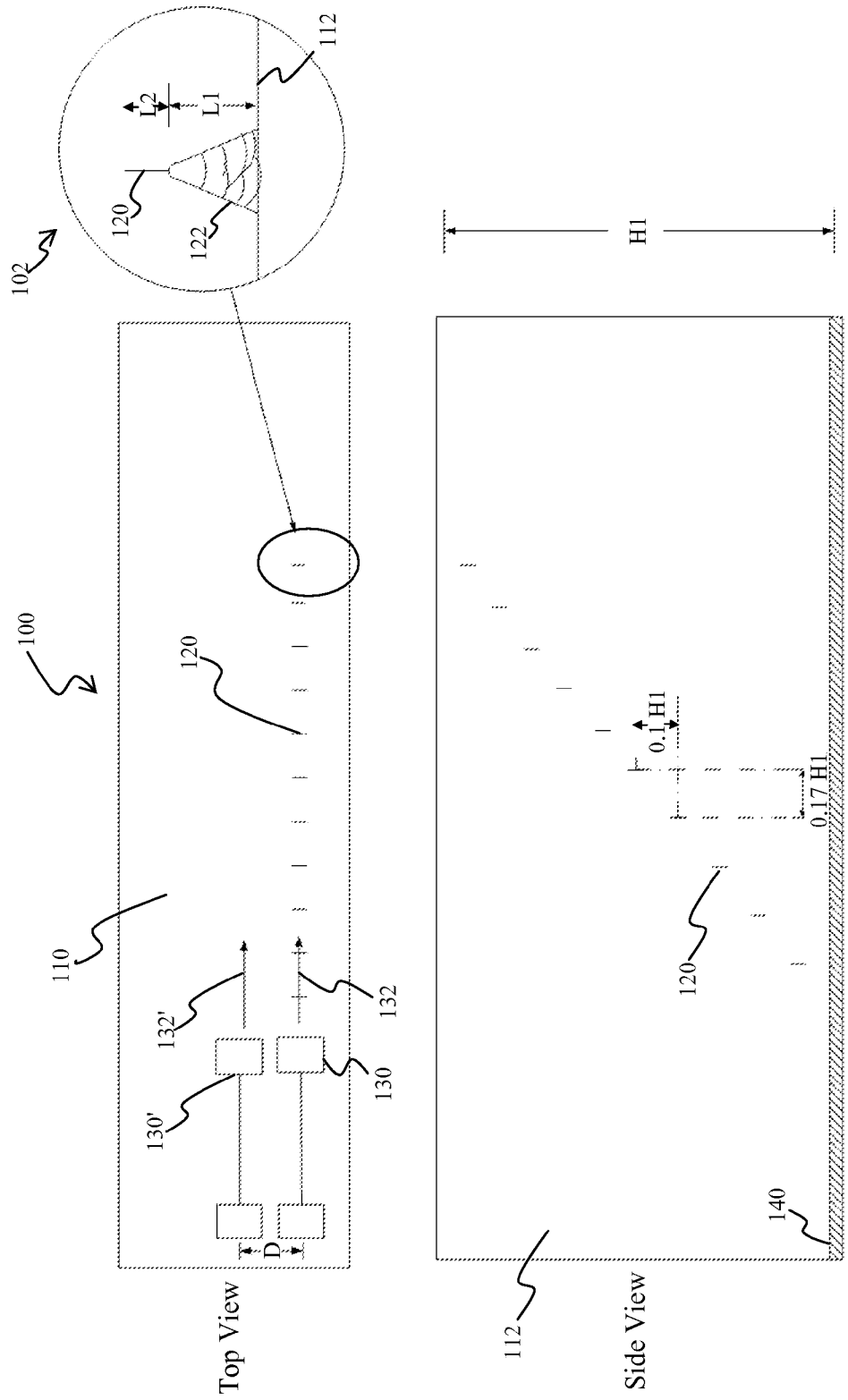
FIG. 1 is an exemplary schematic illustration of a TOFD sensitivity block according to the inventive subject matter.

In one particularly preferred aspect of the inventive subject matter, multiple defects are formed in the test block material, wherein the defects are characterized by their generally non-circular, and most preferably flat geometry. For example, such defects can be produced by electrical discharge machining (EDM), which allows the formation of simulated cracks having dimensions that replicate the dimensions of known reheat cracks. FIG. 1 illustrates one exemplary ultrasound TOFD reference block 100, where the top top view of the block is above the side view of the same block. Here, block 100 is formed from carbon steel and has a top surface 110 that includes a first test path 132 and a second test path 132' for the TOFD setup 130 and 132' respectively (in most cases, the setup 130 and 132' is the same). The top surface is typically wide enough to accommodate both test paths next to each other. Thus, D (the distance between the test paths) will typically be at least 0.5 times, and more typically at least 1.0 times the width of the transducer or setup. Test path 132 is typically located such that at least some (and more preferably all) of the notches 120 are perpendicularly below the test path 132. Furthermore, it is noted that the test path in most embodiments will typically be planar, but curved and test paths also deemed suitable. Where multiple test paths are employed, it is contemplated that the distance between test paths will typically be at least equivalent to a transducer width (however, the distance may be less in some cases). Regardless of the relative positioning, the test path(s) may be marked on the block by engraving, print, or other indicia. Where desired, the block may also include an overlay 140.

While not limiting to the inventive subject matter, it is generally preferred that the (EDM) notches are formed in at least one side 112 of the test block 100 to a depth that is at least equal to the width of the transducer element width. To separate the notch from the edge of the block (which could cause signal interference), a groove can be machined over a portion of the notch. The groove is then at least partially filled in by welding the portion that is in excess of the desired flaw size. Inset 102 depicts one exemplary detail view of such notch formation. Here, notch 120 is first formed in the side 112 of the block to a depth of L1+L2, and a groove is then formed over the notch to a depth L1. Weld filler 122 is then used to fill the groove as shown in 102. Thus, the notch 120 will have a length L2 and is offset into the block material by a length L1. It should be appreciated that in some circumstances near side detection of reheat cracks may be limited by interference from the lateral wave generated with the TOFD technique. To accommodate for such interference, a notch is placed relatively close to (e.g., within 6 mm) of the surface, but is separated from the surface by at least a short (e.g., 2 mm) ligament. Where needed, near-surface sensitivity can be demonstrated through the response obtained using a creeping wave technique or via recognition of disruption patterns in the lateral wave.

With respect to the notches it is generally contemplated that the notches need not necessarily have the same orientation, and that different orientations of notches are also suitable. For example, contemplated blocks may have a plurality of notches that have a difference in angle of 5 degrees to so allow assessment of notches that are not transverse to the test path (simulated weld). Furthermore, while notch formation via EDM is generally preferred, it should be appreciated that the notches may also be formed using various alternative processes, including laser micromachining, electrochemical micromachining, etc. Thus, it should be appreciated that the notch size and/or geometry may vary considerably. However, it is generally preferred that the notch geometry is typically flat (i.e., each of the two dimensions (width, depth) are at least 2-times, more typically at least 5 times, and most typically 10 times larger than the remaining dimension (thickness)). It is still further contemplated that while preferred notches are generally planar, alternative notch geometry is also deemed suitable, including curved, angled, and irregular geometries.

Similarly, the number of notches may vary, but it is generally preferred that the block has at least several notches, typically evenly distributed across the height of the block. With respect to positioning of the notches, it is generally preferred that the notches are placed such that interference of signals from two or more notches is avoided. However, relatively close proximity of at least two notches is not expressly excluded (e.g., to provide example for signals obtained from adjacent cracks). With respect to the orientation of the notches relative to the test path it should be noted that the notches need not always be transverse and normal to a plane parallel to the test path. Indeed, all variations (deviation from transverse and/or normal of between, e.g., 1 and 30 degrees, between 30 and 60 degrees, or between 60 and 90 degrees) from the transverse and normal position are expressly included herein. Suitable notch sizes will typically be reflective of the size of reheat cracks, however, smaller and larger sizes are also contemplated herein. Therefore, preferred notches will have a smallest dimension between 100 micron and 2 mm, and a largest dimension that is typically less than 2 cm (e.g., between 2 mm and 8 mm).

It is especially preferred that the notches are arranged in the block in a step wise manner (when viewed from the side, e.g., at vertical increments and lateral offset of about 10% of block height H1) to so reduce signal interference from multiple notches. Moreover, positioning of multiple notches in a step-wise fashion will also allow correlation of TOFD signals with known positions of defects with known geometry. For example, it is preferred that the sensitivity/demonstration block will have EDM notches placed at each 10% of simulated wall thickness (height of block) with a lateral offset (horizontal distance between notches measured along scan path) by 15% to 20%. While other placements are also deemed suitable, it is especially preferred that the offset is selected such as to move the adjacent flaw out of the path of received or transmitted sound which may interfere with or attenuate the signal (e.g., a 10% placement with 10% offset will put the adjacent flaw at 45 degrees, which is the primary sound path for most typical examination set ups. By placing the notch at least 15% offset the adjacent flaw will be oriented at >65 degrees. If 70 degree probes are used then the lateral offset should be at least 20% of thickness or twice the vertical spacing). Thus, a typical vertical offset will be between 8-12% of height of block, and a lateral offset between 12-25% of the height of the block.

Signals from the demonstration block are then compared against each other for a given TOFD set up. When signals from notches yield an amplitude less than 20% (or other desired sensitivity level) of the strongest signal, they should be considered outside the limit of coverage of the set up and additional set ups may be necessary to provide complete coverage. Furthermore, it should be noted that by simply running additional scans offset in increments equal to the width of the transducer element, lateral area of coverage can also be determined. Viewed from a different perspective, it should be noted that the resultant flaw will have a desired size (i.e., reflecting a typical reheat crack) and will be centered on the transducer path while being separated from the edge of the block. Therefore, the block will also allow correlation of TOFD signals with known positions of defects with known geometry.

Figure 2:
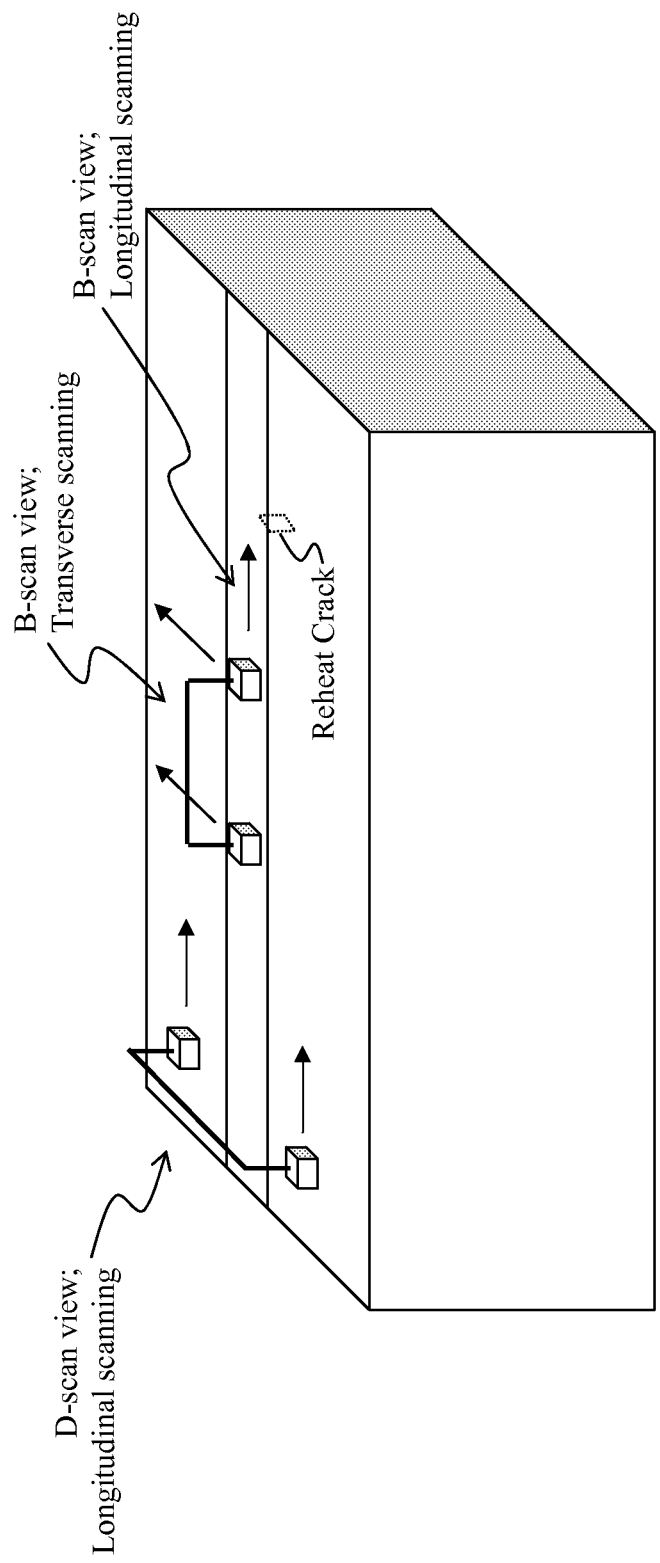
FIG. 2 schematically depicts the difference between B- and D-scan views of TOFD scans in different directions.

FIG. 2 depicts the difference between longitudinal TOFD scanning (D-scan view) and transverse TOFD scanning (B-scan view) in which the transducers operate in pitch-catch mode. It should be especially appreciated that the TOFD sensitivity blocks and methods according to the inventive subject matter provide numerous advantages and overcome the difficulties inherent in current code mandated blocks. First, as EDM notches are formed rather than holes drilled, the simulated defects now have a size that is comparable to presently known reheat cracks (e.g., 4 mm×4 mm although smaller notches may be possible). Second, the EDM notches are generally planar (or otherwise non-round) and will so allow to minimize reflected energy and to maximize diffracted energy, thereby providing a signal output that is more comparable to that of actual reheat cracks. Similarly, as the EDM notches are also transversely oriented (non-parallel) relative to the direction of the sound beam and the scanning direction, signal output that is more comparable to that of actual reheat cracks. Third, as the EDM notches are arranged in a step-wise fashion, individual signals can be assessed without clutter from adjacent notches.

Consequently, it should be particularly recognized that contemplated blocks and methods will be suitable for any B-scan TOFD application, and other ultrasonic testing (e.g., phased array response) for defects having a generally flat geometry. With respect to the material of the testing blocks it is contemplated that the block will typically be formed from a material that is identical or similar to those intended to be tested (e.g., steel, carbon steel, stainless steel, etc). Moreover, it should be appreciated that the particular size and shape of the TOFD block is not limiting to the inventive subject matter and different sizes and geometries are deemed suitable for use herein. However, it is generally preferred that the TOFD block is generally configured as a rectangular block.

Thus, specific embodiments and applications of TOFD sensitivity demonstration blocks have been disclosed. It should be apparent, however, to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

What is claimed is:

1. An ultrasound time-of-flight diffraction (TOFD) reference apparatus, comprising:
   a mass of material having an optionally planar first surface defining a test path, and a second surface;

wherein the apparatus further has a third surface opposite the first surface and a height defined by a distance between the first and third surfaces, and wherein first and third surfaces are parallel;

a plurality of flat notches formed below the second surface such that the flat notches extend within the mass of material and are disposed below the first surface; and wherein at least one of the flat notches has a transverse and normal orientation relative to the test path.

2. The apparatus of claim 1 wherein a welded fill is disposed between the at least one of the plurality of flat notches and the second surface.

3. The apparatus of claim 1 wherein the at least one of the flat notches has a thickness of less than 1 mm and a depth and height of less than 5 mm×5 mm.

4. The apparatus of claim 1 wherein the plurality of flat notches are arranged in a stepwise manner along the second surface.

5. The apparatus of claim 1 wherein the plurality of flat notches have a vertical offset of between 8-12% of the height and a horizontal offset of between 12-25% of the height.

6. The block of claim 1 wherein the test surface is a planar surface.

7. The block of claim 1 wherein the block is formed from a steel.

8. A method of forming an ultrasound time-of-flight diffraction (TOFD) reference block, comprising:

forming a test surface on a mass of material;

forming a plurality of flat notches in a second surface within the mass of material such that the notches are perpendicularly disposed below the test surface;

wherein at least one of the flat notches has a transverse and normal orientation relative to the test path;

forming a groove in at least a portion of the at least one of the notches or forming a groove and then forming the at least one of the notches in the groove; and filling the groove with a weld material.

9. The method of claim 8 wherein the flat notches are formed by electrical discharge machining, laser micromachining, or electrochemical micromachining.

10. The method of claim 8 wherein the flat notches are arranged in a stepwise manner.

11. The method of claim 8 wherein the notches are arranged relative to each other such that a second notch does not interfere with a signal to or from a first notch.

12. The method of claim 8 wherein the block has a further surface opposite the test surface and a height defined by a distance between the test surface and further surface, and wherein the test surface and further surface are parallel.

13. The method of claim 12 wherein the flat notches have a vertical offset of between 8-12% of the height and a horizontal offset of between 12-25% of the height.

14. The method of claim 8 wherein the at least one of the flat notches has a thickness of less than 1 mm and a depth and height of less than 5 mm×5 mm.

\* \* \* \* \*